United States Patent [19]
Johnson et al.

[11] Patent Number: 5,484,890
[45] Date of Patent: * Jan. 16, 1996

[54] ANTIHEMOPHILIC FACTOR STABILIZATION

[76] Inventors: Alan J. Johnson, 127 W. 12th St., New York, N.Y. 10011; Anne J. Fulton, 515 Avon Dr., East Windsor, N.J. 08520

[*] Notice: The portion of the term of this patent subsequent to Jan. 11, 2011, has been disclaimed.

[21] Appl. No.: 138,481

[22] Filed: Oct. 15, 1993

Related U.S. Application Data

[63] Continuation of Ser. No. 790,390, Nov. 12, 1991, Pat. No. 5,278,289.

[51] Int. Cl.$^6$ .......................... C07K 1/18; C07K 14/755
[52] U.S. Cl. ........................................ 530/383; 530/416
[58] Field of Search ........................... 435/184; 530/380, 530/383, 416

[56] References Cited

U.S. PATENT DOCUMENTS

| | | | |
|---|---|---|---|
| 2,833,691 | 5/1958 | Klaas et al. | 530/416 |
| 3,803,115 | 4/1974 | Fekete et al. | 530/383 |
| 4,264,471 | 4/1981 | Briggs et al. | 530/416 |
| 4,361,509 | 11/1982 | Zimmerman et al. | 530/383 |
| 4,388,232 | 6/1983 | Eibl | 530/383 |
| 4,508,709 | 4/1985 | Amphlett et al. | 530/383 |
| 4,522,751 | 6/1985 | Linnay et al. | 530/383 |
| 4,743,680 | 5/1988 | Mathews et al. | 530/383 |
| 4,847,362 | 7/1989 | Mathews et al. | 530/383 |
| 4,952,675 | 8/1990 | Mathews et al. | 530/383 |
| 4,965,203 | 10/1990 | Silbering et al. | 435/214 |
| 4,970,300 | 11/1990 | Fulton et al. | 530/383 |
| 5,043,428 | 8/1991 | Heimburger et al. | 530/383 |
| 5,278,289 | 1/1994 | Johnson et al. | 530/383 |

FOREIGN PATENT DOCUMENTS

| | | | |
|---|---|---|---|
| 0018353 | 10/1980 | European Pat. Off. | |
| 0127025 | 12/1984 | European Pat. Off. | |
| 321835 | 6/1989 | European Pat. Off. | 530/383 |

OTHER PUBLICATIONS

Jane Gitschier et al., "Characterization of the Human Factor VIII Gene", *Nature* 312(22):326–330, Nov. 1984.

Wiliam I. Wood et al, "Expression of Active Human Factor VIII from Recombinant DNA Clones", *Nature* 312(22):330–337, Nov., 1984.

John J. Toole et al., "Molecular Cloning of a cDNA Encoding Human Antihaemophilic Factor", *Nature* 312(22):342–347, Nov., 1984.

V. J. Marder et al., "Standard Nomenclature for Factor VIII and Von Willebrand Factor: A Recommendation by the International Committee on Thrombosis and Haemostasis", *Thrombosis and Haemostasis (Stuttgart)* 54(4):871–872, 1985.

Jan Over et al., "Survival of 125 Iodine–Labeled Factor VIII in Normals and Patients with Classic Hemophilia", *J. Clin. Invest.*, pp. 223–234.

Carol A. Edwards et al., "Tri(n–Butyl) Phosphate/Detergent Treatment of Licensed Therapeutic and Experimental Blood Derivatives", *Vox Sang* 52:53–59, 1987.

Edward G. D. Tuddenham, "The Properties of Factor VIII Coagulant Activity Prepared by Immunoadsorbent Chromatography", *J. Lab. Clin. Med.* 93(1), pp. 40–54, Jan., 1979.

John W. Fenton, "Human Thrombosis", *J. Bio. Chem.* 252(11):3587–3598, 1977.

(List continued on next page.)

*Primary Examiner*—Jeffrey E. Russel
*Attorney, Agent, or Firm*—Darby & Darby

[57] ABSTRACT

A method of recovering a purified and stabilized protein having antihemophilic factor activity (Factor VIII), from a biological sample containing Factor VIII, at least one destabilizing protease impurity, i.e. thrombin, and optionally one or more proprotease impurity, is provided. The biological sample is contacted with a protease removing and/or inhibiting agent, thereby inhibiting and/or removing the destabilizing protease impurity. The method provides increased yield and resolution of Factor VIII. Also provided are purified and stabilized Factor VIII non-lyophilized, liquid in compositions.

4 Claims, 1 Drawing Sheet

OTHER PUBLICATIONS

H. J. Weiss, "A study of the Cation– and pH–Dependent Stability of Factors V and VIII in Plasma", *Thrombosis et diathesis Haemorrhagica* XIV(12):33–51, 1965.

E. G. Tuddenham et al. "Human Factor VIII Procoagulant Protein" (1982).

Mae B. Hultin et al., "The Activation and Inactivation of Human Factor VII by Thrombin: Effect of Inhibitors of Thrombin", *Blood*, 57(3):476–482, Mar. 1981.

R. Carr et al., "Abnormalities of Circulating Lymphocyte Subsets in Haemophiliacs in an AIDS–Free Population", *The Lancet*, pp. 1431–1434, Jun. 30, 1984.

J. Niemetz et al., "Activated Coagulation Factors: In–Vivo and in–Vitro Studies", *Brit J. Haemat.* 16:337–351, 1969.

G. A. Rock et al., "Stability of VIII:C in Plasma: The Dependence on Protease Activity and Calcium", *Thrombosis Research* 29:521–535, 1983.

P. R. Foster et al., "Improving Yield in the Manufacture of VIII Concentrates", *Scand J. Haematol. Supp.* 40, 33:103–110, 1984.

Carol A. Fulcher et al., "Thrombin Proteolysis of Purified Factor VIII Procoagulant Protein: Correlation of Activation with Generation of a Specific Polypeptide", *Blood* 61(4):807–811, Apr. 1983.

Gordon A. Vehar et al., "Structure of human factor VIII", *Nature* 312(22):337–342, Nov. 1984.

Frances Rotblat et al., "Purification of Human Factor VIII:C and Its Characterization by Western Blotting Using Monoclonal Antibodies", *Biochemistry* 24:4294–4300, 1985.

"Factor VIII Degradation Products in Heated Concentrates", *The Lancet*, pp. 1448–1449, Jun. 21, 1986.

Carol A. Fulcher et al., "Characterization of the Human Factor VIII Procoagulant Protein with a Heterologous Precipitating Antibody", *P.N.A.S., USA* 79:1648–1652, Mar., 1982.

Alan J. Johnson et al., "Studies on the Purification and Characterization of VIII:C" (1982).

J. J. Morgenthaler, "Chromatography of Antihemophilic Factor on Diaminoalkane– and Aminoalkane–Derivatized Sepharose", *Thromb Haemostas (Stuttgart)* 47(2):124–127, 1982.

Roger L. Lundblad et al., "The Effect of Dextrose on Chromatography of Antihemophilic Factor (Factor VIII)", *Thrombosis Research* 1:197–200, 1972.

Harvey J. Weiss, "Von Willebrand Factor: Dissociation form Antihemophilic Factor Procoagulant Activity", *Science*, 18:1149–1151, Dec., 1973.

Leon W. Hoyer, *Plasma Coagulation Factors*, "Factor VIII", Chptr. 4, 1987.

Carol A. Fulcher et al., "Human Factor VIII Procoagulant Protein", *J. Clin Invest.* 76:117–124, Jul. 1985.

Dan Eaton et al., "Proteolytic Processing of Human Factor VIII. Correlation of Specific Cleavages by Thrombin, Factor Xa, and Activated Protein C with Activation and Inactivation of Factor VIII Coagulant Activity", *American Chemical Society*, pp. 505 . 512, 1986.

C. Orthner "Characterization of Proteases in AHF Concentrates", Mar. 11, 1985, J. Lab Clin Med., vol. 104, No. 5, 1984, pp.816–828.

ANTIHEMOPHILIC FACTOR STABILIZATION

This is a continuation of application Ser. No. 07/790,390, filed Nov. 12, 1991, now U.S. Pat. No. 5,278,289.

FIELD OF THE INVENTION

This invention relates to a method of recovering a purified and stabilized protein having antihemophilic factor activity (AHF or Factor VIII) from a biological sample containing Factor VIII, at least one destabilizing protease impurity, and optionally one or more proprotease impurity. The biological sample is contacted with at least one protease removing and/or inhibiting agent to remove or to inhibit destabilizing factor(s) in the sample. The stabilization method may be used in conjunction with any of the commonly used fractionation methods to increase yields and resolution of antihemophilic Factor VIII (VIII:c) resulting in higher recovery of stable, moderate or high purity antihemophilic factor concentrates for clinical use.

BACKGROUND OF THE INVENTION

The process of blood clotting begins with an injury to a blood vessel. The damaged vessel wall initiates hemostasis by causing adherence and accumulation of platelets at the point of vascular injury and by activating the plasma proteins which initiate the coagulation process. Sequential activation, via specific proteolytic cleavages and conformational changes, of a series of proteins (including Factor VIII) initiate a coagulation cascade that eventually leads to deposition of insoluble fibrin. The fibrin, together with aggregated platelets, curtails the escape of blood through the point of injury in the damaged vessel wall.

One of these coagulant proteins, Factor VIII, is a plasma protein that has the ability to correct the clotting defect in plasma from patients with Hemophilia A. The activity of Factor VIII is also measured by its ability to induce clotting in plasma obtained from these patients. One unit of Factor VIII is defined as the amount of Factor VIII present in one milliliter of normal, adult male plasma. This standard is a World Health Organization standard and is available from the National Institute for Biological Standards and Control, Holly Hill, Hampstead, London NY3 6RD, England.

During normal blood coagulation, Factor VIII is activated by thrombin, a protease, which affects a proteolytic modification (cleavage) of Factor VIII. (Weiss et al., *Science*, 182: 1149–1151, 1973; Hoyer, Chapter 4, *Hemostasis and Thrombosis*, 2d Ed., Colman, Ed., J. B. Lippincott & Co., Philadelphia, Pa., 1987; Fulcher et al., *J. Clin. Invest.*, 6: 117–124, 1985; and Eaton et al., *Biochemistry*, 25: 505–512, 1986) Following an initial increase in activity after exposure of Factor VIII to thrombin, there is a decay in activity to below base line levels. This decay in activity is attributed to further proteolytic cleavage of activated Factor VIII by thrombin, instability of the partially cleaved molecules Hultin, M. B. et al., *Blood*, 57: 476–482, 1981, and during pathological states, to inactivation by thrombin-activated protein C (Eaton, D. et al., *Bioch.* 25: 505, 1986). The activation and inactivation of Factor VIII by thrombin and protein C allows a fine measure of control over coagulant activity in vivo. Unfortunately, it may also cause premature degradation and instability of Factor VIII, and particularly of the isolated, purified Factor VIII or purified plasma fractions containing Factor VIII, prior to its administration to mammalian hosts in need of such treatment.

The primary therapeutic use of Factor VIII has been its intravenous administration to patients with hemophilia A to stop or to prevent bleeding. Early administration was by the infusion of whole blood or fresh-frozen plasma. These methods required the infusion of very large volumes of proteins and long infusion times, often causing hypervolemia.

The use of plasma cryoprecipitate ("cryo") eliminated the need for whole blood or fresh frozen plasma infusion but the moderate volumes and high protein concentrations still required long infusion times. The cryo was not completely soluble, the cryo solution used for infusion required filtration, and the cryo's AHF content was low and highly variable. Moreover, cryo required storage at −20° C. in large plastic blood bags, and therefore, required large refrigeration facilities.

The primary source of native Factor VIII used today to treat those in need of clotting factor is still plasma, and the use of lyophilized, higher purity Factor VIII concentrates has solved many of the above problems. However, the yield obtained by conventional methods of purification is relatively low, making the cost of the factor excessive. Furthermore, some of the low purity concentrates contain high amounts of contaminating proteins including specific blood-type antibodies that cause hemolysis, proteins that cause immunological abnormalities including a temporary inversion of the T-cell ratio (helper/suppressor) which resembles AIDS (Carr, R. et al., *Lancet* 1: 1431, 1984), fibrinogen, fibronectin, von Willebrand factor, and other proteins.

When a clinical Factor VIII concentrate shows evidence of prior activation, several in vitro and in vivo problems may occur. If the Factor VIII assay was performed by a one stage procedure, it may be falsely high (Niemitz and Nossel, *Brit. J. of Hematol.* 16: 337, 1969); this is not the case, if the assay is performed by a two stage procedure, but very few laboratories are equipped to use the method. Additionally, the activated material is unstable and tends to lose activity during short term storage in the liquid state and during long term storage in the lyophilized state, resulting in poor results when infused in vivo. Use of these Factor VIII concentrates could lead to inadequate treatment for the patient and excessive bleeding.

Substantial activation of antihemophilic factor in plasma and cryoprecipitate is usually prevented by the addition of citrate as the blood is drawn. However, the addition of too much citrate at the time of drawing or later in the purification procedure can cause inactivation of Factor VIII and a corresponding decrease in yield (Rock, et al., *Thromb.* Res. 29: 521–535, 1983, Foster, P. R. et al., *Scan. J. Haematol.* Supp. 40, 33: 103–110, 1984). Consequently, heparin and calcium are often added to the cryoprecipitate or the partially purified Factor VIII during fractionation. In addition, most of the contaminating procoagulant clotting factors or proproteases which are present, such as Factor II, VII, IX and X, and protein C, are adsorbed with aluminum hydroxide. However, it is difficult, if not impossible, to adsorb all of the contaminating Factors II, VII, IX, and X and protein C with aluminum hydroxide without also adsorbing Factor VIII. For example, when Factors II, VII, IX and X are adsorbed from cryoprecipitate or plasma with 5 to 20% aluminum hydroxide and the residual cryoprecipitate or plasma is brought to approximately 3 mM $Ca^{++}$, coagulation still occurs in a relatively short period. It was believed that this was due to residual Factors II, VII, IX, and X in the preparation.

Additionally, minute amounts of thrombin tend to form during blood collection and during large scale cryoprecipitation. When Factor VIII is purified and concentrated, some thrombin is purified and concentrated in addition. The effects of various proteolytic enzymes, including thrombin on purified Factor VIII, were shown by Eaton et al. Bioch. 25: 505 (1986), and the activation of Factor VIII by thrombin with redistribution of polypeptide chains in Factor VIII was demonstrated by polyacrylamide gel electrophoresis by Fulcher et. al., *Blood* 61: 807–811, (1983), Vehar et al., *Nature*, 312, 337–342 (1984), and Rotblatt et al., *Biochem.* 24: 4294–4300 (1985). Similar biochemical changes were found in commercial Factor VIII concentrates purified by large scale methods for clinical use when analyzed by polyacrylamide gradient autoradiograms of Factor VIII-Factor VIII antibody complexes (Barrowcliffe, *Lancet.*, 1: 1448–1449 (1986).

Chromatographic techniques, including ionic, hydrophobic, and immunoaffinity chromatography, have been used to purify Factor VIII, but the yield is relatively low. Several groups of investigators have purified Factor VIII with specific activities as high as 3,000 units per milligram of protein (Fulcher et al., *Proc. Natl. Acad. Sci. USA*, 79: 1648–1652, (1982); Tuddenham, et al., *NIH Symposium on Factor VIII/von Willebrand Factor*, pg. 1., Scripps Clinic and Research Foundation, La Jolla, Calif. (1982); Johnson et al., *NIH Symposium on Factor VIII/von Willebrand Factor*, pg. 2., Scripps Clinic and Research Foundation, La Jolla, Calif. (1982).

Much effort has been made to increase the purity of Factor VIII concentrates. This included the use of immunoaffinity chromatography and monoclonal antibodies (Fulcher et al., *Proc. Natl. Acad. Sci. USA*, 79: 1648–1652 (1982) and Zimmerman et al., U.S. Pat. No. 4,361,509. Overall recovery was estimated to be less than 15% without a heating step.

Further attempts were described by J. J. Morgenthaler, *Thromb. Haemostas*, 47(2): 124 (1982) wherein the use of acetate-glycine-lysine buffer on modified sepharose columns to purify Factor VIII:C from polyethylene glycol precipitated AHF was disclosed.

The addition of 0.05M dextrose in the eluting buffer of bovine Factor VIII during ion exchange column chromatography (on DEAE-cellulose) slightly improved the purity of the product and increased the yield as reported by Lundblad et al. *Thrombosis Research*, 1: 197, Pergamon Press, Inc. (1972). However, resolution was sightly reduced.

Purification of Factor VIII by column chromatography in the presence of additives, including sugars and polyhydric alcohols which serve to increase the electrostatic forces on the surface of the proteins while decreasing the hydrophobicity of the proteins, was reported to result in high recovery of preparations having high purity and resolution (Mathews et al., U.S. Pat. Nos. 4,743,680, 4,847,362, and 4,952,675).

Fulton et al., U.S. Pat. No. 4,970,300, disclose conjugates of proteins having antihemophilic factor activity linked to non-antigenic ligands. These conjugates were stated to have a longer half-life than unconjugated proteins while maintaining substantial Factor VIII activity. Fulton et al. also used short columns of ionic resins to remove residual amounts of Factors II, VII, IX and X.

Finally recombinant Factor VIII has become available through the cloning of the Factor VIII gene. (Gitschier, et al. *Nature* 312: 326–330 (1984); Wood et al., *Nature* 312: 330–337, 1984; Vehar et al., *Nature*, 312: 337–342, (1984); and Toole, et al., *Nature*, 312: 342, (1984).

A novel method for stabilizing partially purified Factor VIII and Factor VIII from biological fluids or mixtures of cellular products derived from recombinant materials, often containing calf serum and/or endopeptidases, has now been discovered. This method prevents activation or degradation of moderately, or highly purified Factor VIII during viral inactivation, purification, recovery, lyophilization and storage and produces a higher yield from the starting material in vitro and a higher recovery in vivo. This results, in turn, in a safer, more effective therapeutic agent at lower cost.

SUMMARY OF THE INVENTION

In accordance with the present invention, there is provided a method of recovering a purified and stabilized protein having antihemophilic factor activity from a biological sample which comprises the protein having antihemophilic factor activity, at least one destabilizing protease impurity, and optionally one or more proprotease impurity. The method comprises contacting the sample with an amount of at least one protease inhibiting and/or removing agent effective to inhibit and/or remove a destabilizing amount of the protease impurity.

A preferred embodiment of the invention comprises recovering a protein having antihemophilic factor activity which is suitable for human clinical use from the sample. The method comprises contacting the sample with an amount of at least one protease inhibiting agent effective to inhibit a destabilizing amount of the protease impurity without further removal of inhibited protease, inhibiting agent, or a combination thereof.

A further preferred embodiment comprises contacting the sample with an amount of at least one protease removing agent effective to remove a destabilizing amount of the protease impurity.

Another embodiment of the invention comprises extracting Factor VIII from the sample with extraction buffer, adding an anti-coagulant and fibronectin/fibrinogen precipitant, such as heparin, to yield a precipitate and a supernatant, adsorbing the supernatant with aluminum hydroxide, optionally precipitating the supernatant with NaCl/glycine, optionally reconstituting the resultant precipitate in extraction buffer, inactivating any viral contaminants, treating the sample as above to recover Factor VIII, and optionally concentrating the Factor VIII further by diafiltration and ultra filtration against a high salt content final buffer.

Also contemplated by the invention is a non-lyophilized liquid composition comprising a purified and stabilized protein having antihemophilic factor activity substantially free of destabilizing protease impurity.

DETAILED DESCRIPTION OF THE INVENTION

A novel process for the purification and stabilization of proteins having antihemophilic factor activity is provided. These proteins are purified from biological samples. The present inventors have found that protease impurities cause instability of Factor VIII isolates, that partially purified samples from which Factor VIII is to be derived or Factor VIII isolates may be treated with protease inhibiting and/or removing agents, and that this treatment will vastly improve Factor VIII stability and purity.

The term "biological sample" is defined herein as biological fluids ant mixtures of cellular products derived from recombinant materials.

The term "biological fluid" is defined herein as any solution or suspension medium which contains or can contain a protein without causing its permanent denaturation or inactivation, including but not limited to plasma, urine, tissue culture media, physiological solutions, and the like.

The term "protein having anti-hemophilic activity" as defined herein as Factor VIII or antihemophilic factor (AHF), an activating coagulation glycoprotein, is further defined as:

A. Factor VIII activity (VIII:C), i.e. the functional property of normal plasma, absent in the plasma of patients with severe classic hemophilia, that is measured in a standard coagulation assay; or B. Factor VIII antigen (VIII:AG), i.e. antigenic determinants on Factor VIII:(C) measured by immunoassays carried out with human antibodies.

The above definition corresponds to the standard definition of Factor VIII recommended by the International Committee on Thrombosis and Hemostasis (Marder et al., *Thromb. Hemostasis*, 54: 871–872, (1985).

Factor VIII includes, individually or collectively, human, porcine, or other mammalian Factor VIII and/or fragments of these proteins displaying Factor VIII activity and/or such proteins and/or active fragments thereof produced by recombinant techniques.

The term "stabilized protein having antihemophilic activity" or "Factor VIII" is defined herein as an AHF protein that has not been prematurely, fully or partially activated, inactivated, or denatured, and therefore, degraded to the degree that it cannot be stored in the liquid state for a reasonable period of time, i.e. 24 hours or more and preferably 48 hours or more, under typical storage conditions known to those of ordinary skill in the art, for subsequent clinical use. It should also be emphasized that earlier clinical investigation of partially or fully activated Factor VIII showed that it had a very short disappearance time when infused in man, while "stabilized" or non-activated Factor VIII had a disappearance time of 8–12 hours (Over et al., *J. Clin. Invest.*, 62: 223–234 (1978)).

The term "recovering" includes, but is not limited to, isolating Factor VIII fractions which are free of quantities of impurities sufficient to cause destabilization.

Partially activated or fully activated Factor VIII is extremely labile and partial activation of Factor VIII frequently occurs when AHF is purified by conventional methods of fractionation. As explained above, Factor VIII is very sensitive to minute quantities of thrombin, a naturally occurring protease necessary for normal clotting; but minute quantities of thrombin are a frequent impurity in Factor VIII isolates. When present, thrombin cleaves and degrades the Factor VIII molecule and activates the contained protein C. The activated protein C, in turn, inactivates Factor VIII by further cleaving of the molecule.

Typically, Factor VIII may be purified from plasma cryoprecipitate as illustrated in Table I below. The precipitate is first extracted with a buffer to solubilize the Factor VIII and other proteins. The precipitate is discarded, and heparin is added to the supernatant to serve as an anticoagulant and to precipitate most of the fibronectin and fibrinogen. Aluminum hydroxide, along with most of the optional calcium ion, is then added to adsorb major portions of the procoagulant Factors II, VII, IX and X and protein C. Factors II, VII, IX and X and protein C contain negatively charged γ-glutamic amino acids, and all tend to be adsorbed onto aluminum hydroxide gels. Sodium chloride/glycine is optionally added to precipitate partially purified Factor VIII, and the resultant precipitate is solubilized and incubated with Tween 80 and TNBP to inactivate viral contaminants such as hepatitis A, hepatitis B, HIV (Edwards et al., *Vox. Sang.*, 52, pp. 53–59 (1987)) and the like. The incubated supernatant is then purified further, by methods known to those of ordinary skill in the art such as adsorption by ion exchange chromatography, preferably using quaternary amino methyl (QMA) and/or quaternary amino ethyl (QAE) resin adsorbents to purify Factor VIII and to eliminate the Tween 80, TNBP, and residual procoagulant factors. Diafiltration and ultrafiltration may then be used to bring the ionic composition to final formulation and to concentrate the Factor VIII further. The Factor VIII product is about 7500 times purified from plasma (about 100 units per milligram of protein).

METHOD FOR THE PURIFICATION OF HUMAN FACTOR VIII FROM CRYOPRECIPITATE

However, these "purified" samples, particularly purified cryoprecipitates, even though adsorbed on aluminum hydroxide and chromatographed using an ion exchange column, still tend to become partially activated and consequently degraded when eluted from the column.

It was previously thought that this was the result of juxtaposition and concentration on the column of negatively charged Factors II, IX, and X and protein C as well as negatively charged Factor VIII.

Therefore, researchers performed studies to determine the requisite conditions for the prevention of activation and to remove the residual strongly negatively charged proprotease or procoagulation Factors II, VII, IX and X and protein C. These studies were carried out using anion exchange chromatography as a model system because of its sensitivity to nanogram quantities of contaminating coagulant and/or procoagulant molecules which are already activated or become activated and subsequently degrade Factor VIII. Because the Factor VIII in most Factor VIII concentrates is present in only very small amounts (nanograms per ml) and because the total charge on the Factor VIII molecule is only weakly negative, the Factor VIII required at least 20 times more ion exchange resin for adsorption than Factors II, VII, IX, and X and protein C. Therefore, after aluminum hydroxide adsorption, preferential adsorption of residual amounts of Factors II, VII, IX and X, and protein C was performed, without removing more than about 1 to 5% of the Factor VIII, by applying relatively small amounts of anionic (QMA or QAE) resin in the form of a small "guard column". See, Fulton, et al., U.S. Pat. No. 4,970,300. Other suitable anionic resins include diethylamino ethyl (DEAE) groups on silicate, cellulose, or agarose resins.

Further preferential adsorption of the contaminant Factors II, VII, IX and X and protein C from samples purified according to the procedure described in Table I above, augmented by these small amounts of either anionic QAE or QMA resins, however, did not stabilize the Factor VIII fractions. In addition, assays for procoagulant or coagulant proteins did not disclose or identify the destabilizing factor.

However, it was discovered in the present invention that the instability of Factor VIII could be prevented by: (a) one or more non-specific protease inhibitors, such as trasylol (preferably from about 3 to about 30 u/ml, and most preferably about 10 u/ml); benzamidine (preferably from about 0.1 to about 10mM, and most preferably about 1 mM); diphenyl fluorophosphate (DFP) (preferably from about 0.2 to about 20 mM and most preferably about 2mM); phenyl methyl sulfonyl fluoride (PMSF), (preferably from about 0.1 to about 30 mM, and most preferably 5 mM); and p-amidino-phenyl-methane-sulfonyl fluoride, (PAPMSF), (preferably from about $10^{-7}$ to about $10^{-3}$M, and most preferably about $10^{-5}$M) ; (b) one or more specific thrombin inhibitors, such as antithrombin-III (AT III) (preferably from about 0.1 u to about 50 u/ml, and most preferably about 10 u/ml) alone or in combination with heparin (preferably from about 2 to about 200 u/ml, and most preferably about 5 u/ml), hirudin or hirudin peptides (preferably from about 0.1 u to about 100 u/ml and most preferably about 5 u/ml); dansyl-arginine-4-ethyl piperidine amide (DAPA) (preferably from about $10^{-7}$M to about $10^{-3}$M, and most preferably about $10^{-5}$m); D-phenyl-alanyl-prolyl-arginine chloromethyl ketone (PPACK) (preferably from about $10^{-9}$ to $10^{-4}$M, and most preferably about $10^{-6}$M); or (2R,4R)4-methyl-1-n-(3-methyl-1,2,3,4-tetrahydro-8-quinoline-sulfonyl)-L-arginyl-2-piperidine-carboxylic acid (compound 805), (preferably from about $10^{-9}$ to about $10^{-4}$M, and most preferably about $10^{-6}$M); or (c) any combination of any of the foregoing.

While DFP alone and heparin alone has been used by others (Tuddenham, et al., *J. Lab. Clin. Med.*, 93, 40–53, 1979), DFP, PMSF, p-APMSF and DAPA are very toxic, and in our laboratory, heparin alone was unable to inhibit the protease activity or its destabilizing effects in moderately pure Factor VIII unless additional AT-III was added. Therefore, it was concluded by the present inventors that amounts of pre-formed thrombin which were too small to be assayed caused the residual instability and that treatment during the Factor VIII recovery and purification process with a protease inhibiting or removing agent, and specifically a thrombin inhibiting or removing agent, would greatly increase the stability of recovered Factor VIII.

It was also noted that because the isoelectric points of thrombin are 7, 7.3, and 6, thrombin has a well defined anion binding exosite (Fenton et al., *J. Biol. Chem.*, 252, 3587, 1977), and cationic ion exchange resins may be used to purify thrombin, thrombin should be and was readily adsorbed to negatively charged groups such as cationic ion exchange resins.

The sample can be contacted with the protease or thrombin inhibiting agents at any stage of isolation or purification as long as the impurity to be inhibited is contacted or inhibited before premature activation or inactivation of Factor VIII occurs. Preferably, an inhibiting agent is added in an amount effective to inhibit the protease or thrombin so that its presence is reduced to an amount too small to initiate destabilization or premature activation and inactivation and subsequent degradation of Factor VIII. Contacting can be performed by any method known to those of ordinary skill in the art, including but not limited to mixing in a vibromixer, passage over a column containing a protease inhibitor, or the like.

Similarly, the sample can be contacted with the protease or thrombin removing agent at any stage. The sample can be contacted by any means known to those of ordinary skill in the art and preferably by ion exchange chromatography. Preferred chromatography resins are cationic resins, particularly those rich in carboxyl methyl groups including, but not limited to, carboxymethyl silicate, carboxymethyl cellulose, carboxymethyl agarose or a combination thereof. Stronger cation exchange resins with sulfopropyl or other groups may be used but the strong acidic groups or the matrix used for some of these resins such as acrylic resins, may adsorb additional proteins, including Factor VIII. Preferred columns have a pK ranging from about 3.5 to about 4.5 and preferably of about 4.

The volume of cation exchange resin necessary in the method of the present invention is far less than the amount of anion exchange resin typically used in the purification of Factor VIII. The amount of anionic resin typically ranges from about 50 to about 20,000 ml. Preferably, it is ⅕ to ¹⁄₅₀ the volume typically used in the anion exchange column, and most preferably it is about ¹⁄₂₀ the volume. Similarly, the weight of cation exchange resin is far less than the weight of anion exchange resin typically used in purification. Preferably, it is about ¹⁄₂₅ to about ¹⁄₄₅ the weight and most preferably is about ¹⁄₄₀ the weight typically used for the anion exchange column. The typical weight of anionic resin used ranges from about 25 to about 10,000 grams. Typical column chromatography methods and parameters for columns which may be used in conjunction with the present method are detailed for example in Mathews et al, U.S. Pat. Nos. 4,743,680, 4,847,362 and 4,952,675 and in Fulton et al., U.S. Pat. No. 4,970,300.

Furthermore, protease or thrombin inhibiting agents and removing agents can be used in combination either sequentially or simultaneously. When used sequentially their use may be interrupted by one or more other steps or procedures, but it is preferable that the inhibiting agent be used first.

A typical isolation procedure according to the present invention is illustrated in Table 2 below. The preliminary and final steps are similar to those in Table 1 above, but the sample is either treated with a protease or thrombin inhibiting and or removing agent prior to, concurrently with, or subsequent to final fractionation, and preferably after treatment with aluminum hydroxide.

TABLE 2

CURRENT FACTOR VIII PURIFICATION METHOD FROM CRYOPRECIPITATE

| Step | Description |
|---|---|
| 1. Extract FVIII from cryoprecipitate (4.5:1–5:1 v/w, 25° C., 15'–20') | Extraction buffer: 20 mM tris; .0025 trisodium citrate; pH 7.5; If buffer is about 30° C. before adding to cold cryo, the final t° will be about 25°). Use vibromixer or Silverson mixer. |
| 2. (a) Add 80 U heparin/ml of extract (25° C.) | Mix with vibromixer 10'–15' during slow addition of heparin (5000 u/ml) and during pH change with acetate buffer. (2 M sodium acetate plus acetic acid, 80 U heparin/ml, pH 5.3) |
| (c) Adsorb with 10% Alhydrogel (Aluminum Hydroxide (25° C.) Centrifuge (25° C.) | Mix with vibromixer for 15'–20' |
| *3. Weigh supernatant, add NaCl/ glycine buffer (1:2.05 w/w; 30° C.) Centrifuge (30° C.) | Mix for 10' with NaCl/glycine buffer: (3.6 M NaCl, 2.1 M glycine, .02 M citrate, 2 mM $Ca^{++}$, pH 7.0) |
| *4. Reconstitute in .2–.3 volume tris/ citrate buffer to 10 mg/ml protein (25–30° C.) | Tris/citrate buffer: (0.2 M tris, .0025 M citrate, pH 7.0) If this step is used as a stop-over, and the material is frozen, NaCl may be added to produce an equivalent conductance of <.15 M. |
| - CHROMATOGRAPHY - | |
| 5. Viral inactivation | Add 20% Tween 80 to a final concentration of 1% followed by 100% TNBP to a concentration of 0.3% and mix for 6 hours or more at 24° C. at 10 mg protein/ml (dilute with buffer as in step 4, if necessary). No adsorption of TNBP with oil is required before chromatography. |
| 6. Adjust ion concentration of sample - | Dilute with .02 M Tris, pH 7.4 to an equivalent conductance of (.15 M NaCl, if necessary |
| 7. Equilibrate column(s) | 3 volumes of equilibration buffer: (0.1 M NaCl; 0.02 M Tris; 1 M Sorbitol, pH 7.4 with 1 N HCl) |
| 8. Treat sample with protease inhibitors or Put sample through first (CM) column | AT III, APMSF, P.Pack, etc. and/or 1.25 g CM Accell + 1.25 g QMA Accell. |
| 9. Main column Ratio of column d:h is about 1:1) | Main column, 25 g QMA Accell, maximum loading 750 mg-protein). Protein load, 14–15 mgs protein per ml QMA in main column. |
| 10. Washing main column (25° C.) | a. 2 volumes of equilibration buffer b. 5 volumes of first wash buffer: (0.2 M NaCl; 0.02 M Tris; 1 M Sorbitol; pH 7.4). |
| 11. Elution from column (25° C.) | 2 volumes of eluting buffer: (0.35 M $CaCl_2$; 0.02 M sodium acetate; 10% glycerol v/v; 5% EtOH v/v; pH 6.0) |
| 12. Test for stability by incubating sample | Dialyse (2 ml sample vs 500 ml buffer) in presence of .25% human serum albumin against (0.3 M NaCl; 0.02 M Tris; 12 mM sodium citrate; 1.5 mM calcium chloride; pH 7.0) |
| *13. Dia-filter and concentrate in mini-tan apparatus *Optional | Diafilter and concentrate against final buffer formulation |

DESCRIPTION OF PREFERRED EMBODIMENT

The following examples are intended to illustrate the invention without limiting its scope.

EXAMPLE 1

(AT III)

Factor VIII was extracted from cryoprecipitate with extraction buffer (20 mM tris, 0.0025M trisodium citrate, 4.5:1–5:1 v/w, pH 7.5) at 25° C. for 15 to 20 minutes in a vibromixer or a Silverson mixer. The extract was washed with 2.5% polyethylene glycol (PEG). 5000 units of heparin per ml of extract were mixed in over 10 to 15 minutes in a vibromixer, and pH was adjusted to 5.3 with acetate buffer (2M sodium acetate plus acetic acid, 80 u heparin/ml, pH 5.3). The precipitate was adsorbed with 10% aluminum hydroxide (Alhydrogel) in a vibromixer for 15 to 20 minutes at 25° C. and was centrifuged at 5000×g and 25° C. for 20 minutes.

The supernatant was weighed and was precipitated with sodium chloride/glycine buffer (3.6M NaCl, 2.1M glycine, 1:2.05 w/w, 0.02M citrate, 2 mM $Ca^{++}$, pH 7.0) was added. The mixture was centrifuged at 10,000×g and 30° C. for 30 minutes. The fraction was reconstituted in 0.2 to 0.3 volumes of tris/citrate buffer (0.02M tris, 0.0025M citrate, pH 7.0) to 10 mg protein/ml at 25° to 30° C.

20% Tween 80 was added to a final concentration of 1% and 100% TNBP was added to a final concentration of 0.3%. The solution was mixed for at least 6 hours at 24° C. at 10 mg protein/ml to eliminate viral activity.

Ion concentration was adjusted to an equivalent conductance of less than 0.15M NaCl by dilution with 0.02M tris, pH 7.4.

Thrombin was inactivated by mixing with 10 u of AT III.

A main ion exchange chromatography column (25 g QMA Accell, d:h≈1:1) was equilibrated with 3 volumes of equilibration buffer (0.1M sodium chloride, 0.02M Tris, 1M Sorbitol, pH adjusted to 7.4 with 1N HCl). The sample was put through the column at a protein load of 14–15 mg protein/ml QMA. The main column was washed at 25° C. with 2 volumes of equilibration buffer, 5 volumes of first wash buffer (0.2M NaCl, 0.02M tris, 1M Sorbitol, 5% EtOH, pH 7.4), and finally, 2 volumes of second wash buffer (0.175M NaCl, 0.02M sodium acetate, pH 7.4). The column was eluted with two volumes of eluting buffer (0.35M $CaCl_2$, 0.02M sodium acetate, 10% glycerol v/v, 5% EtOH v/v, pH 6.0). The recovered protein was diafiltered against the final buffer formulation.

The stability of the eluted protein was tested after dialysis overnight at 24° C. by placing a 2 ml sample vs. 500 ml buffer (0.3M NaCl, 0.02M tris, 12 mM sodium citrate, 1.5 mM $CaCl_2$, pH 7.0) in the presence of 0.25% human serum albumin.

Several runs were performed.

Figure 1:
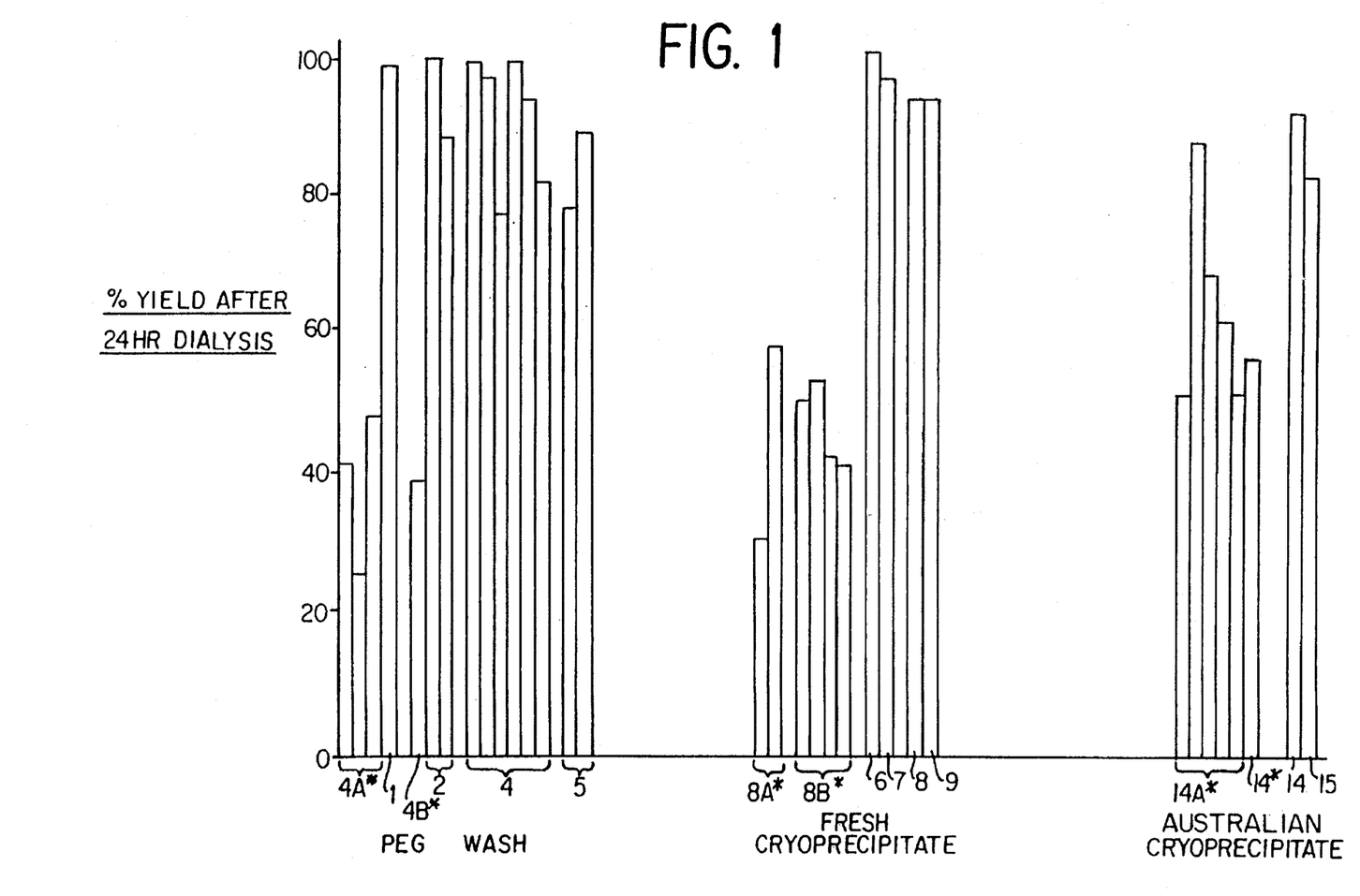
FIG. 1 is a graphic representation of Factor VIII stability after treatment of the fractionated Factor VIII by various reagents.

Representative results are illustrated in Table 3 and in FIG. 1.

TABLE 3

FACTOR VIII (AT III)

| RUN | YIELD (%) | PURITY (Factor VIII-u/mg) | OVERNIGHT STABILITY (Dialysis 24° C.) (%) |
|---|---|---|---|
| 1 | 56 | — | 100 |
| 2 | 91 | 83 | 89 |
| 3 | 83 | — | 105 |
| 4 | 44 | 17 | 107 |

EXAMPLE 2

(AT III and QMA)

The procedure of Example 1 was followed, except before being put through the main column, the sample containing AT III was run through a first column containing 1.25 g of QMA Accell that had been equilibrated with 3 volumes of equilibration buffer. Several runs were performed.

Representative results are illustrated in Table 4 and in FIG. 1.

TABLE 4

FACTOR VIII (AT III/QMA)

| RUN | YIELD (%) | PURITY (Factor VIII-u/mg) | OVERNIGHT STABILITY (Dialysis 24° C.) (%) |
|---|---|---|---|
| 1 | 91 | 83 | 89 |
| 2 | 83 | — | 105 |
| 3 | 44 | 17 | 107 |

EXAMPLE 3

(PPack and QMA)

The procedure of Example 2 was followed, substituting $10^{-6}$M of P.Pack/ml for the AT III.

Yield was 65%, purity was 26 U Factor VIII/mg, and stability was 98%.

EXAMPLE 4

(CM/QMA)

The procedure of Example 2 was followed except the addition of AT III was eliminated and the first column contained 1.25 g of CM Accell and 1.25 g of QMA Accell. Several runs were performed.

Representative results are illustrated in Table 5 and in FIG. 1.

TABLE 5

FACTOR VIII (CM/QMA)

| RUN | YIELD (%) | PURITY (Factor VIII-u/mg) | OVERNIGHT STABILITY (Dialysis 24° C.) (%) |
|---|---|---|---|
| 1 | 49 | — | 100 |
| 2 | 57 | — | 98 |
| 3 | 85 | 42 | 78 |
| 4 | 54 | 51 | 103 |
| 5 | 40 | 36 | 82 |
| 6 | 36 | 20 | 95 |
| 7 | 47 | 49 | 83 |

COMPARATIVE EXAMPLE 4A*

(No AT III)

The procedure of Example 1 was followed, eliminating the addition of AT III. Several runs were performed.

Representative results are illustrated in Table 6.

TABLE 6

FACTOR VIII (ONLY MAIN COLUMN)

| RUN | YIELD (%) | PURITY (Factor VIII-u/mg | OVERNIGHT STABILITY (Dialysis 24° C.) (%) |
|---|---|---|---|
| 1 | 40 | 20 | 31 |
| 2 | 36 | 25 | 59 |
| 3 | 46 | 24 | — |
| 4 | 28 | 17 | — |
| 5 | 46 | 165 | 43 |
| 6 | 46 | 63 | 27 |
| 7 | 16 | 12 | 57 |

COMPARATIVE EXAMPLE 4B*

(QMA)

The procedure of Example 2 was followed, eliminating the addition of AT III. Several runs were performed.

Representative results are illustrated in Table 7 and in FIG. 1.

TABLE 7

FACTOR VIII (QMA)

| RUN | YIELD (%) | PURITY (Factor VIII-u/mg | OVERNIGHT STABILITY (Dialysis 24° C.) (%) |
|---|---|---|---|
| 1 | 45 | 60 | 46 |
| 2 | 56 | 25 | 51 |
| 3 | 52 | 27 | 54 |
| 4 | 54 | 28 | 43 |

TABLE 7-continued

| | FACTOR VIII (QMA) | | |
|---|---|---|---|
| RUN | YIELD (%) | PURITY (Factor VIII-u/mg) | OVERNIGHT STABILITY (Dialysis 24° C.) (%) |
| 5 | 35 | 29 | 42 |
| 6 | 29 | 20 | — |

EXAMPLE 5

(PPack, CM/QMA)

The procedure of Example 2 was followed substituting $10^{-6}$M of PPack for the AT III and substituting a first column of 1.25 g (CM) carboxymethyl cellulose Accell and 1.25 g QMA Accell for the first column. Several runs were performed.

Representative results are illustrated in Table 8 and FIG. 1.

TABLE 8

| | FACTOR VIII (CM/QMA/PPack) | | |
|---|---|---|---|
| RUN | YIELD (%) | PURITY (Factor VIII-u/mg) | OVERNIGHT STABILITY (Dialysis 24° C.) (%) |
| 1 | 52 | 27 | 94 |
| 2 | 73 | 38 | 78 |

EXAMPLE 6

(AT III/QMA)

The procedure of Example 2 was followed, eliminating the polyethylene glycol wash.
Results are illustrated in FIG. 1.

EXAMPLE 7

(PPack, QMA)

The procedure of Example 3 was followed, eliminating the polyethylene glycol wash.
Results are illustrated in FIG. 1.

EXAMPLE 8

(CM/QMA)

The procedure of example 4 was followed, eliminating the polyethylene glycol wash.
Results are illustrated in FIG. 1.

COMPARATIVE EXAMPLE 8A*

(No AT III)

The procedure of Comparative Example 4A* was followed, eliminating the polyethylene glycol wash. Two runs were performed.
Results are illustrated in FIG. 1.

COMPARATIVE EXAMPLE 8B*

(No AT III)

The procedure of Comparative Example 4B* was followed, eliminating the polyethylene glycol wash. Several runs were performed.
Results are illustrated in FIG. 1.

EXAMPLE 9

(PPack, CM/QMA)

The procedure of Example 5 was followed, eliminating the polyethylene glycol wash.
Results are illustrated in FIG. 1.

EXAMPLE 10

(CM/QMA)

The procedure of Example 4 was followed substituting heparin precipitated cryproprecipitate for the cryoprecipitate. Several runs were performed.
Representative results are illustrated in Table 9.

TABLE 9

| | FACTOR VIII (CM/QMA) | | |
|---|---|---|---|
| RUN | YIELD (%) | PURITY (Factor VIII-u/mg) | OVERNIGHT STABILITY (Dialysis 24° C.) (%) |
| 1 | 67 | 374 | 98 |
| 2 | 75 | 239 | 102 |
| 3 | 81 | 67 | 103 |
| 4 | 81 | 106 | 98 |
| 5 | 42 | 71 | 83 |

EXAMPLE 11

(CM/QMA)

The procedure of Example 4 was followed with cryoprecipitate made on a production scale. Several runs were performed.
Representative results are illustrated in Table 10.

TABLE 10

| | FACTOR VIII (PRODUCTION SCALE-CM/QMA) | | | | | |
|---|---|---|---|---|---|---|
| | PRE CM/QMA COLUMN | | POST CM/QMA & POST QMA COLUMNS | | OVERALL | |
| RUN | YIELD (%) | (U/mg Protein) | YIELD (%) | (U/mg Protein) | YIELD (%) | (U/mg Protein) |
| 1 | 83 | 1.2 | 71 | 85 | 59 | 85 |
| 2 | 68 | 2.12 | 69 | 110 | 47 | 110 |

TABLE 10-continued

FACTOR VIII
(PRODUCTION SCALE-CM/QMA)

| RUN | PRE CM/QMA COLUMN | | POST CM/QMA & POST QMA COLUMNS | | OVERALL | |
|---|---|---|---|---|---|---|
| | YIELD (%) | (U/mg Protein) | YIELD (%) | (U/mg Protein) | YIELD (%) | (U/mg Protein) |
| 3 | 69 | 3.1 | 67 | 374 | 46 | 374 |
| 4 | 69 | 3.1 | 75 | 239 | 52 | 239 |
| 5 | 84 | 2.1 | 76 | 109 | 64 | 109 |
| 6 | 76 | 1.4 | 81 | 67 | 61 | 67 |
| 7 | 71 | 1.7 | 81 | 106 | 57 | 106 |
| 8 | 68 | 1.8 | 70 | 80 | 48 | 80 |
| 9 | 90 | 1.9 | 42 | 71 | 38 | 71 |
| 10 | 69 | 3.9 | 73 | 147 | 50 | 147 |

EXAMPLE 12
(CM/QMA)

The procedure of Example 11 (CM/QMA) was followed substituting frozen cryoprecipitate for the cryoprecipitate. Several runs were performed.

Representative results are illustrated in Table 11.

TABLE 11

FACTOR VIII
(Production Scale - CM/QMA)

| RUN | PRE CM/QMA COLUMN | | POST CM/QMA & POST QMA COLUMNS | | OVERALL | |
|---|---|---|---|---|---|---|
| | YIELD (%) | (U/mg Protein) | YIELD (%) | (U/mg Protein) | YIELD (%) | (U/mg Protein) |
| 1 | 88 | 0.95 | — | — | — | — |
| 2 | 81 | 2.48 | 70 | 176 | 63 | 176 |
| 3 | 81 | 2.48 | 63 | 143 | 57 | 143 |

EXAMPLE 13
(CM/QMA)

The procedure of Example 11 (CM/QMA) was followed eliminating the precipitate with sodium chloride/glycerin buffer. Several runs were performed.

Representative results are illustrated in Table 12.

TABLE 12

FACTOR VIII
(Production Scale - CM/QMA)

| RUN | PRE CM/QMA COLUMN | | POST CM/QMA & POST QMA COLUMNS | | OVERALL | |
|---|---|---|---|---|---|---|
| | YIELD (%) | (U/mg Protein) | YIELD (%) | (U/mg Protein) | YIELD (%) | (U/mg Protein) |
| 1 | 86 | 1.3 | 75 | 101 | 64 | 101 |
| 2 | 86 | 1.7 | 85 | 93 | 73 | 93 |
| 3 | 79 | 1.1 | 66 | 97 | 52 | 97 |

The stability of all the samples of Factor VIII from Examples 11–13 showed a stability after dialysis at 24° C. overnight of between 85 and 103%.

EXAMPLE 14
(CM/QMA)

The procedure of Example 8 was followed, substituting an Australian cryoprecipitate that was over four months old for the cryoprecipitate.

Results are summarized in FIG. 1.

COMPARATIVE EXAMPLE 14A*
(No AT III)

The procedure of Comparative Example 8B* was followed, substituting Australian cryoprecipitate that was over four months old for the cryoprecipitate. Several runs were performed.

Results are summarized in FIG. 1.

EXAMPLE 15

(PPack, CM/QMA)

The procedure of Example 9 was followed, substituting an Australian cryoprecipitate that was over four months old for cryoprecipitate.

Results are summarized in FIG. 1.

EXAMPLE 16

(CM)

The procedure of Example 8 is followed substituting a first column of 2.5 gm of CM only. Yield, purity and stability of the recovered Factor VIII are excellent.

Examples 1–16 when compared with Comparative Examples 4A*, 4B*, 8A*, 8B* and 14A* demonstrate that the removal or inhibition of protease or thrombin from Factor VIII isolates increased yield, purity, and stability on a wide range of cryoprecipitates and a wide range of processing conditions.

All of the above mentioned patents, publications, and test methods are incorporated herein by reference.

Many variations will suggest themselves to those skilled in the art in light of the above detailed description. All such obvious variations are within the full intended scope of the appended claims.

What is claimed:

1. A method of recovering, from a biological sample, an antihemophilic factor protein containing fraction having increased antihemophilic factor protein stability;

said sample comprising (a) an antihemophilic factor protein, (b) at least one destabilizing protease impurity, and (c) at least one proprotease impurity; and said fraction having at least 17 units of antihemophilic factor protein/mg of total protein;

said method comprising:

contacting said sample with an amount of a protease removing agent effective to remove a destabilizing amount of said protease impurity and an amount of proprotease removing agent effective to remove a destabilizing amount of said proprotease impurity;

said proprotease removing agent comprising an anion exchange resin in an amount ranging from 70 mg total loading protein/ml anion exchange resin to 750 mg total loading protein/ml anion exchange resin.

2. A method of recovering, from a biological sample, an antihemophilic factor protein containing fraction having increased antihemophilic factor protein stability;

said sample comprising (a) an antihemophilic factor protein, (b) at least one destabilizing protease impurity comprising thrombin, and (c) at least one proprotease impurity; and said fraction having at least 17 units of antihemophilic factor protein/mg of total protein;

said method comprising:

contacting said sample with an amount of a protease inhibiting or removing agent effective to remove or to inhibit a destabilizing amount of said protease impurity and an amount of proprotease removing agent effective to remove a destabilizing amount of said proprotease impurity;

wherein said protease inhibiting agent comprises one or more thrombin inhibitors selected from the group consisting of antithrombin III, antithrombin III and heparin, p-APMSF, PPack, compound 805, hirudin, DAPA and combinations of any of the foregoing; and said proprotease removing agent comprising an anion exchange resin in an amount ranging from 70 mg total loading protein/ml anion exchange resin to 750 mg total loading protein/ml anion exchange resin.

3. A method of recovering from cryoprecipitate a Factor VIII fraction having increased Factor VIII stability, said cryoprecipitate comprising:

(a) Factor VIII, (b) at least one destabilizing protease impurity, and (c) at least one proprotease impurity, said fraction having at least 17 units of Factor VIII/mg of total protein, said method comprising:

(a) extracting, with an extraction buffer, any Factor VIII, at least one protease impurity, and at least one proprotease impurity from said cryoprecipitate;

(b) adding an anticoagulant and fibronectin/fibrinogen precipitant to yield a precipitate and a supernatant;

(c) adsorbing said supernatant with aluminum hydroxide, (d) precipitating said supernatant with sodium chloride/glycine;

(e) reconstituting the resultant precipitate of step (d) in extraction buffer;

(f) inactivating any viral contaminants in said reconstituted precipitate;

(g) contacting said product of step (f) with an amount of a protease inhibiting or removing agent effective to remove or to inhibit a destabilizing amount of said protease impurity and an amount of proprotease removing agent effective to remove a destabilizing amount of said proprotease impurity;

said proprotease removing agent comprising an anion exchange resin in an amount ranging from 70 mg total loading protein/ml anion exchange resin to 750 mg total loading protein/ml of anion exchange resin;

(h) recovering Factor VIII; and (i) optionally concentrating Factor VIII further by diafiltration and ultrafiltration against a salt containing final buffer.

4. A method as defined in claim 1, wherein said protease removing agent comprises a cation exchange resin.

* * * * *